US012558070B2

(12) United States Patent
Belohlavek

(10) Patent No.: US 12,558,070 B2
(45) Date of Patent: Feb. 24, 2026

(54) SYSTEMS, METHODS, AND MEDIA FOR REAL-TIME SPATIAL TRACKING OF MINIMALLY INVASIVE INSTRUMENTS AND COMPONENTS USING SELECTIVE COLOR DOPPLER MARKERS

(71) Applicant: Mayo Foundation for Medical Education and Research, Rochester, MN (US)

(72) Inventor: Marek Belohlavek, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 625 days.

(21) Appl. No.: 16/973,233

(22) PCT Filed: Jun. 7, 2019

(86) PCT No.: PCT/US2019/036075
§ 371 (c)(1),
(2) Date: Dec. 8, 2020

(87) PCT Pub. No.: WO2019/237013
PCT Pub. Date: Dec. 12, 2019

(65) Prior Publication Data
US 2021/0236093 A1 Aug. 5, 2021

Related U.S. Application Data

(60) Provisional application No. 62/682,334, filed on Jun. 8, 2018.

(51) Int. Cl.
| | |
|---|---|
| *A61B 8/00* | (2006.01) |
| *A61B 8/08* | (2006.01) |
| *A61B 34/20* | (2016.01) |

(52) U.S. Cl.
CPC ............ *A61B 8/488* (2013.01); *A61B 8/0841* (2013.01); *A61B 34/20* (2016.02); *A61B 8/5246* (2013.01); *A61B 2034/2063* (2016.02)

(58) Field of Classification Search
CPC ....... A61B 8/488; A61B 8/0841; A61B 34/20; A61B 8/5246; A61B 2034/2063
See application file for complete search history.

(56) References Cited

U.S. PATENT DOCUMENTS

| | | | |
|---|---|---|---|
| 5,343,865 | A | 9/1994 | Gardineer |
| 8,303,505 | B2 | 11/2012 | Webler |
| (Continued) | | | |

OTHER PUBLICATIONS

Belohlavek, M., et al. A real-time color Doppler marker for echocardiographic guidance of an acoustically active extracorporeal membrane oxygenation cannula. Journal of Ultrasound in Medicine 38.7 (2019): 1875-1885. Available online Nov. 12, 2018.

(Continued)

*Primary Examiner* — Rochelle D Turchen
(74) *Attorney, Agent, or Firm* — Quarles & Brady LLP

(57) ABSTRACT

In some embodiments of the disclosed subject matter, a system for tracking a medical device using color Doppler markers is provided, the medical device can comprise an ultrasound transmitter, and a lead configured to receive a square wave signal from a waveform generator and provide the square wave signal to the ultrasound transmitter causing the ultrasound transmitter to produce acoustic signals. The system can include an ultrasound machine having a display, a transducer that emits color Doppler signals, and a processor, which can be programmed to cause the transducer to emit the color Doppler signals, cause the transducer to detect color Doppler signals generated by an interaction between the emitted color Doppler signals and the acoustic signals, and generate an ultrasound image that includes a color (Continued)

Doppler marker indicative of the presence of the ultrasound transmitter.

16 Claims, 7 Drawing Sheets

(56) References Cited

U.S. PATENT DOCUMENTS

| | | | | |
|---|---|---|---|---|
| 2002/0068951 A1* | 6/2002 | Burbank | ............ | A61B 17/0469 |
| | | | | 606/139 |
| 2004/0267127 A1* | 12/2004 | Abend | ................ | G01S 15/8993 |
| | | | | 600/450 |
| 2009/0118612 A1 | 5/2009 | Grunwald | | |
| 2011/0026364 A1* | 2/2011 | Lee | ........................... | G01S 5/28 |
| | | | | 367/127 |
| 2013/0204138 A1 | 8/2013 | Belohlavek | | |
| 2016/0235485 A1 | 8/2016 | Belohlavek | | |
| 2018/0280680 A1* | 10/2018 | Isaacson | ........... | A61M 25/0068 |

OTHER PUBLICATIONS

Belohlavek, M., et al. Acoustically active injection catheter guided by ultrasound: Navigation tests in acutely ischemic porcine hearts. Ultrasound Med Biol 2014; 40:1650-1659.

Breyer, B. et al. "Ultrasonically marked catheter—a method for positive echographic catheter position identification." Medical & biological engineering & computing 22.3 (1984): 268-271.

Fronheiser, M. P., et al. "Vibrating interventional device detection using real-time 3-D color Doppler." IEEE transactions on ultrasonics, ferroelectrics, and frequency control 55.6 (2008): 1355-1362.

Hatt CR, et al. Mri-3d ultrasound-x-ray image fusion with electromagnetic tracking for transendocardial therapeutic injections: In-vitro validation and in-vivo feasibility. Comput Med Imaging Graph 2013; 37:162-173.

International Searching Authority. International Search Report and Written Opinion for application PCT/US2019/036075. Mailed on Aug. 5, 2019. 17 pages.

Katayama, M., et al. "Acoustically active catheter for intracardiac navigation by color Doppler ultrasonography." Ultrasound in medicine & biology 43.9 (2017): 1888-1896.

Kerut Ek, et al. Technique and imaging for transthoracic echocardiography of the laboratory pig. Echocardiography 2004; 21:439-442.

Kinnick RR, et al. An interposed pad in open-chest echocardiographic porcine scans for mimicking ultrasound signal attenuation in a human chest. J Ultrasound Med 2018; 37:501-509.

Kumar V, et al. Unambiguous identification and visualization of an acoustically active catheter by ultrasound imaging in real time: Theory, algorithm, and phantom experiments. IEEE Trans Biomed Eng 2017.

Landzberg JS, et al. The transponder system: A new method of precise catheter placement in the right atrium under echocardiographic guidance. J Am Coll Cardiol 1988; 12:753-756.

Langberg JJ, et al. The echo-transponder electrode catheter: A new method for mapping the left ventricle. J Am Coll Cardiol 1988; 12:218-223.

Lee MS, et al. A practical guide to the use of echocardiography in assisting structural heart disease interventions. Cardiol Clin 2013; 31:441-454.

Mcmahon EM, et al. Accurate guidance of a catheter by ultrasound imaging and identification of a catheter tip by pulsed-wave doppler. Pacing Clin Electrophysiol 2012; 35:44-50.

US Food and Drug Administration. Information for manufacturers seeking marketing clearance of diagnostic ultrasound systems and transducers: guidance for industry and FDA staff (Table 2-1). Document Issued Sep. 9, 2008. US Food and Drug Administration website. https://www.fda.gov/downloads/UCM070911.pdf. Accessed Dec. 2, 2017.

Vilkomerson D, et al. A system for ultrasonic beacon-guidance of catheters and other minimally-invasive medical devices. IEEE Trans Ultrason Ferroelectr Freq Control 1997; 44:496-504.

Winsberg F, et al. Use of an acoustic transponder for us visualization of biopsy needles. Radiology 1991; 180:877-878.

Zamorano JL, et al. Eae/ase recommendations for the use of echocardiography in new transcatheter interventions for valvular heart disease. Eur Heart J 2011; 32:2189-2214.

Frazin, L. J., et al. "Cannulation of the aortic branches using ultrasound guidance. An animal study." ASAIO Journal (American Society for Artificial Internal Organs: 1992) 43.4 (1997): 321-325.

Frazin, L. J., et al. "Doppler catheter tip localization using color enhancement." Catheterization and cardiovascular diagnosis 32.1 (1994): 62-69.

* cited by examiner

1

SYSTEMS, METHODS, AND MEDIA FOR REAL-TIME SPATIAL TRACKING OF MINIMALLY INVASIVE INSTRUMENTS AND COMPONENTS USING SELECTIVE COLOR DOPPLER MARKERS

CROSS-REFERENCE TO RELATED APPLICATIONS

This application is a 371 U.S. National Phase Entry of International Application No. PCT/US2019/036075, filed Jun. 7, 2019, which claims priority to and the benefit of U.S. Provisional Patent Application No. 62/682,334, filed Jun. 8, 2018, for all purposes as if set forth in its entirety.

STATEMENT REGARDING FEDERALLY SPONSORED RESEARCH

This invention was made with government support under EB019947 awarded by the National Institutes of Health. The government has certain rights in the invention.

BACKGROUND

In general, ultrasonography is often used for guidance of intracardiac and intravascular instruments such as catheters, needles, and cannulas. For example, ultrasonography guidance is often used during transcatheter treatment of valvular heart disease, and myocardial cellular therapy delivered by transendocardial injections. However, image noise and artifacts in grayscale (e.g., B-mode) scans make navigation of minimally invasive imaging tools difficult. Additionally, cardiovascular tissue and minimally invasive tools have similar acoustical properties (such as echogenicity) at frequencies used to perform B-mode scans, which can cause such tools to visually mimic an anatomic structure and, therefore, be difficult to identify and spatially track them in ultrasound images.

Accordingly, systems, methods, and media for real-time spatial tracking of minimally invasive instruments and components using selective color Doppler markers are desirable.

SUMMARY

In accordance with some embodiments of the disclosed subject matter, systems methods, and media for real-time spatial tracking of minimally invasive instruments and components using selective color Doppler markers are provided.

In accordance with some embodiments of the disclosed subject matter, a system for presenting a location of a medical device using color Doppler markers is provided, the system comprising: a medical device comprising: an ultrasound transmitter; and a lead configured to receive a square wave signal from a waveform generator and provide the square wave signal to the first ultrasound transmitter causing the first ultrasound transmitter to produce an acoustic signal having multiple frequency components; an ultrasound machine comprising: a display; a transducer configured to emit a first color Doppler signal; and at least one processor that is programmed to: cause the transducer to emit the first color Doppler signal; cause the transducer to detect a second color Doppler signal generated by an interaction between the first color Doppler signal and the acoustic signal emitted by the ultrasound transmitter; generate an ultrasound image based on the second color Doppler signal, including a first color Doppler marker indicative of the presence of the first ultrasound transmitter; and cause the ultrasound image to be presented by the display In some embodiments, the medical device further comprises: a second ultrasound transmitter; and a second lead configured to receive a second square wave signal from the waveform generator and provide the second square wave signal to the second ultrasound transmitter to produce a second acoustic signal having multiple components; and wherein the processor is further programmed to: cause the transducer to detect a third color Doppler signal generated by an interaction between the first color Doppler signal and the second acoustic signal emitted by the second ultrasound transmitter; and generate the ultrasound image based on the third color Doppler signal, including a second color Doppler marker indicative of the presence of the second ultrasound transmitter.

In some embodiments, the first ultrasound transmitter and the second ultrasound transmitter are configured to generate the first acoustic signal and the second acoustic signal simultaneously.

In some embodiments, a characteristic of the acoustic signal emitted from the ultrasound transmitter varies based on at least one of a frequency and an amplitude of the signal received from the waveform generator.

In some embodiments, the processor is further programmed to: receive an indication that a parameter associated with the first color Doppler signal is to be adjusted, wherein the parameter is one of the following: a gain of the first color Doppler signal; a range of velocities to present in the ultrasound image; a beam penetration depth; a frequency of the first color Doppler signal; a marker size at which to present the first color Doppler marker; a resolution of the ultrasound image; and a frame rate at which to display ultrasound images.

In accordance with some embodiments of the disclosed subject matter, an ultrasound guidance system is provided, the system comprising: a medical instrument having a first ultrasound transmitter coupled to the medical instrument; a waveform generator in communication with the first ultrasound transmitter, the waveform generator configured to: drive the first ultrasound transmitter with a first electrical waveform, the first electrical waveform including a square wave, wherein driving the first ultrasound transmitter with the first electrical waveform causes the first ultrasound transmitter to generate a first acoustic signal, the first acoustic signal having multiple frequency components.

In some embodiments, the first electrical signal is a square wave having a duty cycle in a range of 25% to 75%.

In some embodiments, the first electrical signal has a frequency in a range from 90 to 110 kHz.

In some embodiments, the first electrical signal has a frequency in a range from 100 kHz to 103 kHz.

In some embodiments, the first electrical signal has an amplitude in the range from 0.3 to 9.0 volts peak to peak (Vpp).

In some embodiments, the system further comprises a second ultrasound transmitter coupled to the medical instrument, the second ultrasound transmitter being in communication with the waveform generator.

In some embodiments, the waveform generator is configured to: drive the second ultrasound transmitter with a second electrical waveform, the second electrical waveform being a square wave, wherein driving the second ultrasound transmitter with the second electrical waveform causes the second ultrasound transmitter to generate a second acoustic signal, the second acoustic signal having multiple frequency components.

In some embodiments, the medical instrument is a cannula.

In some embodiments, the cannula has a first port, and a second port, and the first ultrasound transmitter is associated with the first port, and the second ultrasound transmitter is associated with the second port.

In some embodiments, the cannula has a third port, and a third ultrasound transmitter is associated with the third port, the third ultrasound transmitter being in communication with the waveform generator.

In some embodiments, the waveform generator is configured to: drive the third ultrasound transmitter with a third electrical waveform, the third electrical waveform being a square wave, wherein driving the third ultrasound transmitter with the third electrical waveform causes the third ultrasound transmitter to generate a third acoustic signal, the third acoustic signal having multiple frequency components.

In some embodiments, the first, second, and third electrical waveforms each have a waveform frequency, wherein at least two or more of the waveform frequencies are different.

In some embodiments, the first, second, and third electrical waveforms each have a waveform amplitude, wherein at least two or more of the waveform amplitudes are different.

In some embodiments, the waveform generator is coupled to the medical instrument.

In accordance with some embodiments of the disclosed subject matter, an ultrasound guidance system is provided, the system comprising: a waveform generator in communication with a first ultrasound transmitter of an instrument; an ultrasound machine comprising: a display; an ultrasound transducer configured to emit a first color Doppler signal; and at least one processor that is configured to: cause the waveform generator to drive the first ultrasound transmitter with a first electrical waveform, the first electrical waveform being a square wave, wherein driving the first ultrasound transmitter with the first electrical waveform causes the first ultrasound transmitter to generate a first acoustic signal, the first acoustic signal having multiple frequency components; cause the ultrasound transducer to emit a first color Doppler signal; detect a second color Doppler signal from the ultrasound transducer, the second color Doppler signal being formed by an interaction between the first acoustic signal and the first color Doppler signal, the second color Doppler signal being used to form a first color Doppler marker; generate a first ultrasound image that includes the first color Doppler marker using the display; and cause the first ultrasound image to be displayed using the display.

In some embodiments, the ultrasound machine has a gain parameter that controls amplification of the detected second color Doppler signal; and the gain parameter is set in a range from −20 decibels (dB) to −15 dB.

In some embodiments, the ultrasound transducer is configured to emit a first brightness mode (B-mode) acoustic signal, and to receive a second B-mode acoustic signal.

In some embodiments, the at least one processor is configured to: generate the first ultrasound image based on the first color Doppler marker and the second B-mode acoustic signal; and cause the first ultrasound image to be displayed using the display.

In some embodiments, the instrument includes a second ultrasound transmitter, the second ultrasound transmitter in communication with the waveform generator; and wherein the at least one processor is configured to: cause the waveform generator to drive the second ultrasound transmitter with a second electrical waveform, the second electrical waveform being a square wave, wherein driving the second ultrasound transmitter with the second electrical waveform causes the second ultrasound transmitter to generate a second acoustic signal, the second acoustic signal having multiple frequency components.

In some embodiments, the at least one processor is configured to: detect a third color Doppler signal from the ultrasound transducer, the third color Doppler signal being formed by an interaction between the second acoustic signal and the first color Doppler signal, the third color Doppler signal being used to generate a second color Doppler marker; generate a second ultrasound image based on the first color Doppler marker, the second color Doppler marker, and the second B-mode acoustic signal, and wherein the presence of the first color Doppler marker and the second color Doppler marker in the second resultant image indicates a location of the instrument in a scan plane of the ultrasound transducer.

In some embodiments, the first color Doppler marker and the second color Doppler marker are presented using different colors within the second resultant image that correspond to different velocities.

In some embodiments, the spatial relationship of the first color Doppler marker relative to the second color Doppler marker reflects a spatial orientation of the instrument.

In some embodiments, the processor is configured to adjust the color of the first color Doppler marker by adjusting the frequency of the first electrical waveform.

In some embodiments, the processor is configured to adjust the color of the second color Doppler marker by adjusting the frequency of the second electrical waveform.

In some embodiments, the processor is configured to adjust the size of the first color Doppler marker by adjusting the amplitude of the first electrical waveform.

In some embodiments, the processor is configured to adjust the size of the second color Doppler marker by adjusting the amplitude of the second electrical waveform.

In accordance with some embodiments of the disclosed subject matter, a method for detecting and guiding a medical instrument is provided, the method comprising: outputting a first electrical waveform, the first electrical waveform being a square wave; generating a first acoustic signal based on the first electrical waveform; generating a first color Doppler signal; receiving a second color Doppler signal, the second color Doppler signal being formed from the interaction between the first acoustic signal and the first color Doppler signal; generating a first color Doppler marker based on the second color Doppler signal; and generating an ultrasound image that includes the first color Doppler marker.

In some embodiments, generating the first acoustic signal comprises driving an ultrasound transducer with a square wave.

In some embodiments, the first electrical waveform has a duty cycle in a range of 25% to 75%.

In some embodiments, the method further comprises: outputting a second electrical waveform, the second electrical waveform being a square wave; generating a second acoustic signal based on the second electrical waveform; receiving a third color Doppler signal, the third color Doppler signal being formed from the interaction between the second acoustic signal and the first color Doppler signal; and generating a second color Doppler marker based on the third color Doppler signal, wherein the ultrasound image includes the first color Doppler marker and the second color Doppler marker.

In some embodiments, the first color Doppler marker and the second color Doppler marker have different colors in the ultrasound image.

In some embodiments, the first color Doppler marker and the second color Doppler marker have different sizes in the ultrasound image.

BRIEF DESCRIPTIONS OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with various embodiments, mechanisms (which can, for example, include systems, methods, and media) for real-time spatial tracking of minimally invasive instruments and components using selective color Doppler markers are provided.

In accordance with some embodiments of the disclosed subject matter, the mechanisms described herein can be used to track and/or guide minimally invasive instruments using color Doppler ultrasound. In accordance with some embodiments, ultrasound transmitters can be affixed to the minimally invasive instruments, and a waveform with a particular frequency can be supplied to the ultrasound transmitter to cause it to emit ultrasonic waves. In such embodiments, an ultrasound system configured to generate both B-mode and color Doppler images can be used to emit an ultrasonic signal (e.g., using an ultrasound transducer), which can interact with the signals emitted from the ultrasound transmitters affixed to the minimally invasive instruments to generate a signal that can be used to identify the location of the ultrasound transmitter. Acoustic signals from the ultrasound transducer that do not interact with the signals emitted by the ultrasound transmitters affixed to the instrument can be used to generate a gray scale image (e.g., a B-mode scan), while acoustic signals from the ultrasound transducer that do interact can be detected as Doppler shifts by a color Doppler portion of the ultrasound system. In some embodiments, the detected color Doppler shifts can be displayed as part of a color Doppler image, where the location of the ultrasound transmitters can be viewed as real-time color markers on the color Doppler image. In some embodiments, the ultrasound system can display a color Doppler image superimposed on the B-mode image to show location(s) of the ultrasound transmitters (e.g., indicating the location of the portion of the instrument to which the transmitter is affixed). In some embodiments, a user can view the spatial coordinates and/or the orientation of the minimally invasive instrument using the generated color Doppler image (e.g., as real-time color markers) superimposed on the grayscale ultrasound image. The superimposed image allows a user to see both anatomic structures (from the grayscale image) and the location of the minimally invasive instrument (form the color Doppler markers) simultaneously. This permits visual feedback to the user, such that the user can guide the minimally invasive instrument based on the spatial relationship between the anatomical features and the marker(s).

Figure 1:
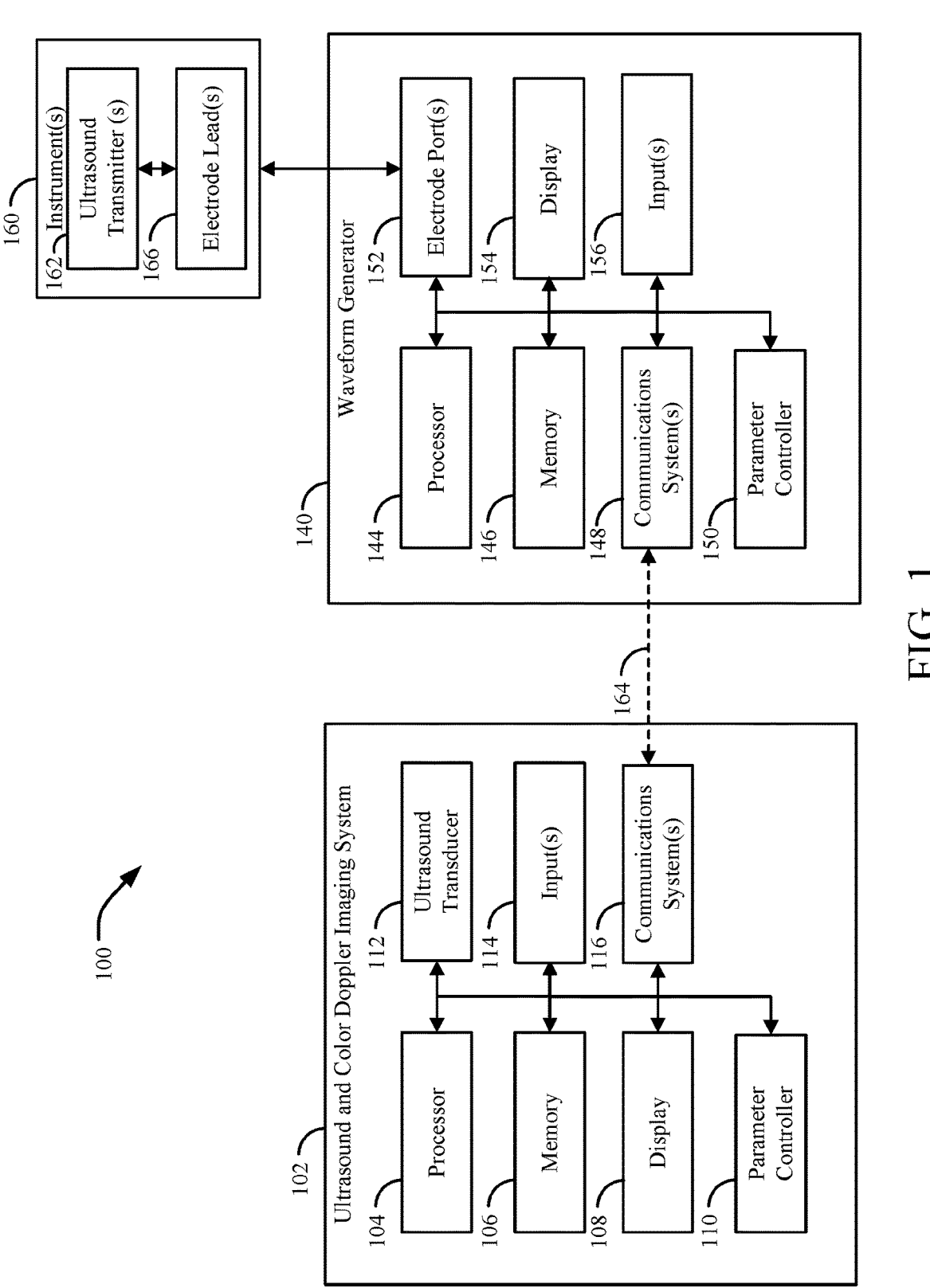
FIG. 1 shows an example of a system for real-time spatial tracking of minimally invasive instruments and components using selective color Doppler markers in accordance with some embodiments of the disclosed subject matter.

FIG. 1 shows an example of an imaging system 100 used for real-time spatial tracking of minimally invasive instruments and components using selective color Doppler markers in accordance with some embodiments of the disclosed subject matter. In some embodiments, system 100 can include hardware that can be used to implement an ultrasound imaging system 102, a waveform generator 140, and a minimally invasive instrument(s) 160 in accordance with some embodiments of the subject matter. In some embodiments, instrument(s) 160 can be any suitable medical instrument such as a cannula, a needle, a surgical tool, an implantable device, and/or a catheter. Additionally, in some embodiments, several ultrasound transmitters 162 could be individually driven by waveform generator 140, which can be implemented with multiple independent channels. Signals of different frequencies can be used to distinguish different ultrasound transmitters 162 by producing color Doppler markers with different (distinctive) colors. In some embodiments, multiple instruments can be individually marked and distinguished in an ultrasound image based on specific ultrasound transmitters 162 that produce marks with different colors. Additionally, in some embodiments, several markers can be used to identify particular components of a single instrument by affixing several separate ultrasound transmitters 162 on that instrument.

As shown in FIG. 1, in some embodiments, ultrasound imaging system 102 can include a processor 104, memory 106, a display 108, a parameter controller 110, an ultrasound transducer 112, one or more inputs 114, and a communications system(s) 116. In some embodiments, memory 106 can include any suitable storage device or devices that can be used to store instructions, values, etc., that can be used, for example, by processor 104 to control the operation of ultrasound imaging system 102, to communicate with waveform generator 140 via communications system(s) 116, etc.

Memory 106 can include any suitable volatile memory, non-volatile memory, storage, or any suitable combination thereof. For example, memory 106 can include random access memory (RAM), read only memory (ROM), electrically erasable programmable read-only memory (EE-PROM), one or more flash drives, one or more hard disks, one or more solid state drives, one or more optical drives, etc. In some embodiments, memory 106 can have encoded thereon a computer program for controlling operation of processor 104.

In some embodiments, display 108 can include any suitable display devices, such as a computer monitor, a touchscreen, a television, a multidimensional visualization system (e.g., virtual reality, augmented reality), etc. Additionally, in some embodiments, display 108 can include any hardware capable of displaying DICOM image data. In some embodiments, parameter controller 110 can be used to adjust one or more parameters of the main ultrasound B-mode and/or color Doppler mode, such as, gain, scale, beam penetration, frequency, marker size, resolution, frame rate, etc. In some embodiments, inputs 114 can include any suitable input devices and/or sensors that can be used to receive user input, such as a keyboard, a mouse, a touchscreen, a microphone (e.g., for receiving voice commands), etc. In some embodiments, ultrasound transducer 112 can include any suitable mechanism for creating acoustic waves (e.g., one or more piezoelectric crystals). In some embodiments, ultrasound transducer 112 can include an array of acoustic generating elements. For example, ultrasound transducer 112 can be one or more phased array transducers. As another example, ultrasound transducer 112 can be one or more linear array transducers.

In some embodiments, processor 104 can be any suitable hardware processor or combination of processors, such as a central processing unit (CPU), a graphics processing unit (GPU), a microcontroller unit (MCU), a microprocessor unit (MPU), etc. In some embodiments, processor 104 can execute at least a portion of the computer program to receive ultrasound parameters via parameter controller 110. In some embodiments, parameter controller can be implemented using display 108 to present a graphical user interface (GUI) configured to receive user input to adjust one or more ultrasound parameters. In some embodiments, ultrasound parameters set via parameter controller 110 can be used to control operation of ultrasound transducer 112. In some embodiments, ultrasound transducer 112 can send and receive acoustic signals related to grayscale ultrasound and/or color Doppler ultrasound. In some embodiments, processor 104 can execute at least a portion of the computer program to receive and store image data values (e.g., grayscale ultrasound or color Doppler) in memory 106. In some embodiments, image data values can be provided to display 108 for presentation of ultrasound images. In some embodiments, the computer program can cause processor 104 to execute at least a portion of process 200 described below in connection with FIG. 2.

In some embodiments, communications system(s) 116 can include any suitable hardware, firmware, and/or software for communicating with waveform generator 140, for communicating information over communication link 164, and/or for communicating over any other suitable communication link and/or communication network(s). For example, communications system 116 can include one or more transceivers, one or more communication chips and/or chip sets, etc. In a more particular example, communications system 116 can include hardware, firmware and/or software that can be used to establish a coaxial connection, a fiber optic connection, an Ethernet connection, a universal serial bus (USB) connection, a Wi-Fi connection, a Bluetooth connection, a cellular connection, etc.

As shown in FIG. 1, in some embodiments, waveform generator 140 can include a processor 144, memory 146, communications systems(s) 148, parameter controller 150, electrode port(s), display 154, and inputs 156. In some embodiments, memory 146 can include any suitable storage device or devices that can be used to store instructions, values, etc., that can be used, for example, by processor 144 to control the operation of the electrode port(s) 152, to communicate with the ultrasound imaging system 102 via communications system(s) 148, etc. Memory 146 can include any suitable volatile memory, non-volatile memory, storage, or any suitable combination thereof. For example, memory 146 can include RAM, ROM, EEPROM, one or more flash drives, one or more hard disks, one or more solid state drives, one or more optical drives, etc. In some embodiments, memory 146 can have encoded thereon a waveform generator program for controlling operation of processor 144. In some embodiments, display 154 can include any suitable display devices, such as a computer monitor, a touchscreen, a television, a segmented liquid crystal display, etc. Alternatively, in some embodiments, display 154 can be omitted (e.g., waveform generator 140 can be implemented using static labels).

In some embodiments, parameter controller 150 can be used to adjust one or more parameters of the voltage/current delivered to the electrode ports. For example, parameter controller 150 can be used to adjust one or more waveform parameters, such as wave type (e.g., a sinusoid, a sawtooth, a rectangular pulse, a square pulse, etc.), frequency, amplitude, phase, time delays (e.g., the voltage/current waveform can be turned on for a period of time and can be turned off for a period of time), duty cycle (e.g., 25%, 50%, 75%) and/or any other suitable parameters. In a more particular example, the wave type can be a square wave having any suitable duty cycle, such as a duty cycle of 25%, 50%, 75%, or any other suitable duty cycle, or could be a narrow pulsed wave (i.e., a very low duty cycle value). In some embodiments, parameter controller 150 can be accessed by activation of input(s) 156. In some embodiments, parameter controller 150 can be controlled via ultrasound imaging system 102 over communication link 164. In some embodiments, parameter controller 150 can be implemented using one or more hardware user interface elements (e.g., hardware buttons, dials, switches, levers, etc.), one or more software buttons (e.g., a hardware button that can be used to interact with a graphical user interface), one or more software user interface elements (e.g., presented as part of a graphical user interface that a user can interact with via input(s) 156). In some embodiments, inputs 156 can include any suitable input devices and/or sensors that can be used to receive user input, such as a keyboard, a mouse, a touchscreen, a microphone, etc.

In some embodiments, processor 144 can be any suitable hardware processor or combination of processors, such as a CPU, a GPU, an MCU, an MPU, a field programmable gate array (FPGA), an application specific integrated circuit (ASIC), etc. In some embodiments, processor 144 can execute at least a portion of the waveform generator program to receive waveform parameters via parameter controller 150. In some embodiments, display 154 can present a graphical user interface (GUI) that can be used to receive user inputs to adjust waveform parameters to parameter controller 150. In some embodiments, parameter controller 150 sends the requested waveform to electrode port(s) 152.

In some embodiments, processor 104 can execute at least a portion of the computer program to execute at least a portion of process 200 described below in connection with FIG. 2.

In some embodiments, communications system(s) 148 can include any suitable hardware, firmware, and/or software for communicating with ultrasound imaging system 102, for communicating information over communication link 164, and/or for communicating over any other suitable communication network(s). For example, communications system(s) 148 can include one or more transceivers, one or more communication chips and/or chip sets, etc. In a more particular example, communications systems 148 can include hardware, firmware and/or software that can be used to establish a coaxial connection, a fiber optic connection, an Ethernet connection, a USB connection, a Wi-Fi connection, a Bluetooth connection, a cellular connection, etc. In some embodiments, communication link 164 can be used to allow the user to adjust ultrasound parameters. In some embodiments, communication link 164 can be used to receive instructions to adjust one or more waveform parameters from ultrasound imaging system 102 (e.g., allowing a user to use ultrasound imaging system 102 to control waveform generator 140). In some embodiments, communication link 164, communications system(s) 148, and/or communications system(s) 116 can be omitted. For example, preexisting ultrasound imaging systems 102 may not be configured with communication system 116 and/or may not be configurable to control other devices (e.g., waveform generator 140). In such an example, implementing waveform generator 140 such that it can be operated manually (e.g., without receiving instructions via communication system 148 over communication link 164) can facilitate use of the mechanisms described herein with a wide variety of conventional ultrasound imaging systems. In some embodiments, waveform generator 140 can be integrated into ultrasound imaging system 102.

As shown in FIG. 1, instrument(s) 160 can be include one or more ultrasound transmitter(s) 162, which can be connected to one or more electrode lead(s) 166. In some embodiments, instrument(s) 160 can be any suitable medical device. In some embodiments, a single electrode lead 166 can be connected to multiple ultrasound transmitters 162, such that the same waveform is supplied to the multiple ultrasound transmitters 162. Additionally or alternatively, in some embodiments, one or more of electrode leads 166 can be connected to just a single ultrasound transmitter 162. In some embodiments, multiple ultrasound transmitters 162 can be affixed to the same instrument 160. In some embodiments, many different types of instruments can be used to implement instrument 160 with ultrasound transmitters and leads, which can be coupled to waveform generator 140. In some embodiments, electrode leads 166 can be electrically connected to electrode ports 152, such that a waveform generated by waveform generator 140 is provided to one or more ultrasound transmitters 162 via a particular electrode lead 166. In some embodiments, ultrasound transmitter 162 can be implemented using one or more piezoelectric crystals. In some embodiments, the piezoelectric crystals can be implemented using lead zirconate titanate. Additionally or alternatively, in some embodiments, the piezoelectric crystals can be implemented to have a unique resonance frequency. However, a piezoelectric crystal can produce acoustic signals in response to a wide range of driving frequencies. For example, a particular piezoelectric crystal that has a resonance frequency around 1 megahertz (MHz) can reliably generate acoustic signals in response to a 100 kHz driving signal, although the frequency response can become unstable outside of a particular range. In some embodiments the acoustic property (or properties) of the piezoelectric crystals can be changed by modifying the materials that surround the piezoelectric crystals (e.g., by encasing a piezoelectric crystal in an epoxy or epoxy-like material). In some embodiments the piezoelectric crystal can be configured to emit acoustic signals in multiple directions (e.g., in the absence of obstructions a crystal can be configured to emit signals nearly omnidirectionally). In some embodiments, ultrasound transmitter 162 can be implemented using piezoelectric crystals available from Sonometrics Corporation of London, Ontario, Canada.

Figure 2:
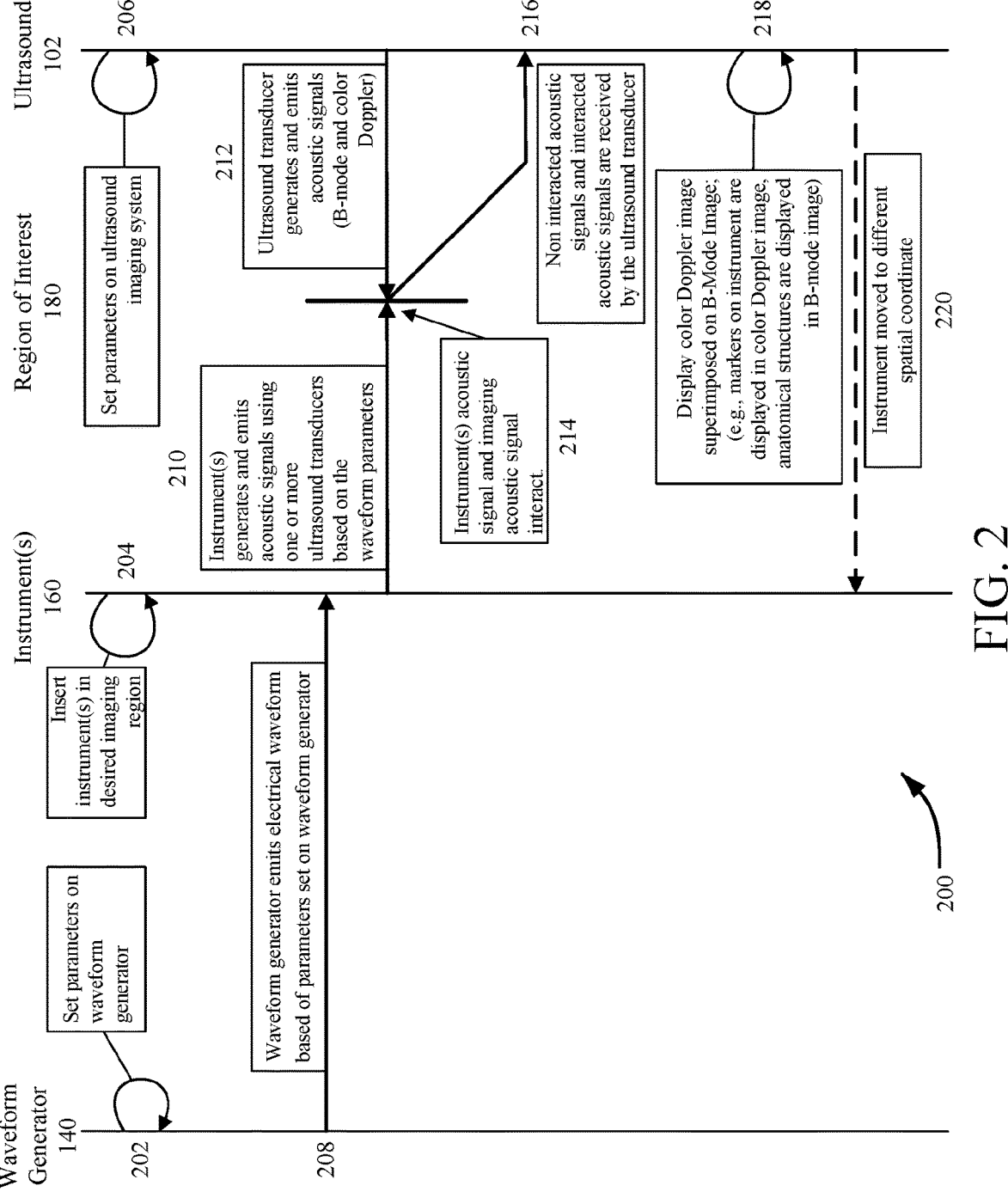
FIG. 2 shows an example of a process for real-time spatial tracking of minimally invasive instruments and components using selective color Doppler markers in accordance with some embodiments of the disclosed subject matter.

FIG. 2 shows an example 200 of a process for real-time spatial tracking of minimally invasive instruments and components using selective color Doppler markers in accordance with some embodiments of the disclosed subject matter. At 202, waveform generator 140 can receive instructions to adjust one or more waveform parameters (e.g., via parameter controller 150 of waveform generator 140). Some examples of different waveform parameters that can be set at 202 are described above in connection with parameter controller 150 of FIG. 1 (e.g. wave type, frequency, amplitude, time delays, etc.). In some embodiments, parameter controller 150 can be controlled from ultrasound system 100 using communication link 164.

At 204, medical instrument 160 can be inserted into a desired imaging region, such as, a blood vessel, an organ, and/or a tissue.

At 206, ultrasound system 102 can receive instructions to adjust one or more parameters of the ultrasound system (e.g., using parameter controller 110 of ultrasound imaging system 102). The parameters adjusted can include gain (e.g., of the receive portion of the color Doppler imaging system), power (e.g., of the transmit portion of the color Doppler imaging system), scale, beam penetration, frequency, marker size, resolution, frame rate, etc. In some embodiments, the gain of the color Doppler can be decreased (e.g., to a range of about −15 decibels (dB) to −20 dB) such that blood flow is not detected by the color Doppler portion of ultrasound system 102 (and therefore is not included in a color Doppler portion of a displayed ultrasound image).

At 208, waveform generator 140 can emit an electrical waveform to the ultrasonic transmitters affixed to the medical instrument, based on the parameters set on the waveform generator at 202. In some embodiments, the waveform generator (e.g., waveform generator 140 of FIG. 1), sends the electrical waveform to the ultrasonic transmitters through an electrical conductor (e.g., electrical leads). In some embodiments, different signals can be provided to different ultrasound transmitters (e.g., via different electrical leads) that can cause different ultrasound transmitters to appear as different colors, to appear at different times (e.g., one or more ultrasound transmitters can be inhibited from receiving signals at certain times). Additionally or alternatively, in some embodiments, waveform generator 140 can provide a modulated signal that can cause the color associated with a particular ultrasound transmitter to change over time in a particular pattern. Such signal modulation can have a variety of uses. For example, signal modulation can be used in addition to, or in lieu of, the color marked to identify a particular ultrasound transmitter. As another example, signal modulation can be used as an additional identifier to further facilitate unambiguous identification of a particular ultrasound transmitter. As yet another example, signal modulation can be used to encode information that can be communicated from the waveform generator (e.g., waveform generator 140) via an ultrasound transmitter (e.g., ultrasound transmitter 162) located on a minimally invasive instrument and an ultrasound imaging system (e.g., ultrasound imaging system 102).

At 210, one or more ultrasound transmitters (e.g., ultrasound transmitter(s) 162) affixed to instrument 160 can generate acoustic signals into the region of interest 180 (e.g., tissue). In some embodiments, the properties of the acoustic signal depend on the electrical waveform delivered to the ultrasound transmitters. For example, changing the amplitude of the electrical waveform can change the amplitude of the emitted acoustic wave. As another example, changing the frequency of the electrical waveform can change the frequency of the emitted acoustic wave. In some embodiments, different waveform shapes can affect the signals emitted by ultrasound transmitter 162. For example, waveform generator 140 can be configured to provide a square wave signal of a particular frequency. As another example, waveform generator 140 can be configured to provide multiple square waves using different channels, and/or multiple waveform generators 140 can be used to provide multiple square waves. In such an example, square wave signals provided over different channels and/or by different waveform generators can have different frequencies, and can be used to feed multiple individual ultrasound transmitters 162 that produce Doppler markers with different colors. In some embodiments, signals emitted by waveform generator 140 can be emitted with any suitable frequency. For example, the square waves can be emitted with a frequency in a range of 90 kHz to 110 kHz, 95 kHz to 105 kHz, 97 kHz to 103 kHz, 97 kHz to 100 kHz, 100 kHz to 103 kHz, etc. Note that this is merely an example, and signals with lower or higher frequencies can be suitable in some cases. The square wave signal-driven ultrasound transmitters 162 produce harmonics that stimulate production of the color Doppler markers. Note that, in some cases, widely spaced driving signal frequencies may cause aliasing of the color Doppler signals. This can cause markers produced from the signals at different frequencies to become indistinguishable from one another (e.g., the colors of the markers can correspond to the same velocity, and consequently produce a marker with the same or a very similar color). In some embodiments, waveform generator 140 can provide square wave signals to ultrasound transmitter(s) 162, which can produce acoustic signals at certain harmonics that interact with transmitted signals from ultrasound transducer 112 to produce new signals that are received by ultrasound transducer 112 and interpreted as Doppler shifts by ultrasound imaging system 102. In such embodiments, driving the same piezoelectric crystal (e.g., used to implement ultrasound transmitter 162) with square waves of different frequencies producing signals with different harmonics. This can provide the ability for a user to control a color of the markers by changing the driving frequency. Note that, in general, the power of the acoustic signal can be related to both the power of the driving signal and the size of ultrasound transmitter 162, with larger crystals being capable of producing acoustic signals with more power.

At 212, ultrasound imaging system 102 can generate acoustic signals using an ultrasound transducer (e.g., ultrasound transducer 112). In some embodiments, the acoustic signal emitted from ultrasound imaging system 102 is a B-mode ultrasonic signal. Additionally or alternatively, in some embodiments, the acoustic signal emitted from the ultrasound imaging system 102 is a color Doppler signal.

At 214, acoustic signals emitted from the ultrasound imaging system can interact with acoustic signals emitted from the ultrasound transmitters affixed to instrument 160 at a region of interest 180 (e.g., acoustic signals from the ultrasound imaging system 102 interacting with acoustic signals emitted by the ultrasound transmitters 162 of the minimally invasive instruments 160). Region of interest 180 can include any spatial region, such as, a region of the subject, an organ, an organ system, a blood vessel, tissue, etc. In some embodiments, the emitted color Doppler acoustic signal can interact in the region of interest with the acoustic signal generated by the ultrasound transducers affixed to medical instrument 160. In some embodiments, the B-mode ultrasonic signal interacts with various structures within the region of interest (e.g., organs, blood vessels, tissue, etc.). In some embodiments the B-mode ultrasonic signal reflects off the various structures and "echoes" back to the ultrasound transducer of the ultrasound imaging system 102 (e.g., ultrasound transducer 112 of ultrasound imaging system 102), which can use the detected signals to generate a B-mode image. In some embodiments, the harmonic acoustic frequencies emitted from the ultrasound transmitter of the medical device interact with the color Doppler acoustic signals.

In some embodiments, when an ultrasound transmitter (e.g., transmitter 162) is driven by a square waveform, the resulting acoustic signals also have higher frequency components (e.g., multiple harmonics) with relatively lower power compared to the power of the square wave. However, square waves generally produce higher power signals than, for example, sine waves due the average power of the square wave being higher holding other variables equal. This can results in higher frequency components maintaining relatively high power, which can interact with the Doppler signal emitted by the ultrasound transducer producing an interacted acoustic signal. The ultrasound transducer can detect at least a portion of the interacted signal as a Doppler shift (e.g., a frequency shift, or a phase shift).

At 216, process 200 can include receiving acoustic signals by the ultrasound imaging system. In some embodiments, the received acoustic signals can include the echo from the interaction with the main ultrasonic signal and the desired area of tissue. In some embodiments, the interacted signal (e.g., the interaction between the emitted color Doppler acoustic signal and the instrument's acoustic signal) is received by the ultrasound. In some embodiments, a calculated signal can be interpreted as a Doppler shift (e.g., based on detecting a frequency shift or phase shift) from the emitted color Doppler signal and the received interacted signal (interaction between the emitted color Doppler acoustic signal and the instrument acoustic signal). In some embodiments, the received signal can be the constructive and/or destructive interference resulting from the two interacted signals (interaction between the emitted color Doppler acoustic signal and the instrument acoustic signal). In some embodiments, the received signal can be a new signal based on the interaction between signals emitted by the ultrasound transmitter (e.g., ultrasound transmitter 162) of the medical instrument and color Doppler acoustic signals (e.g., emitted by ultrasound transducer 112).

At 218, ultrasound imaging system 102 can include the real-time creation of a color Doppler image and a grayscale ultrasound image. In some embodiments, the color Doppler image is superimposed on the grayscale ultrasound image. In some embodiments, the interacted signal from 216 can be viewed on the color Doppler image. The superimposed image allows a user to see both the anatomic structures (from the grayscale image) and the location/orientation of the minimally invasive instrument (form the color Doppler markers) simultaneously.

At 220, the instrument(s) 160 can move to a new spatial location or different orientation based on the relationship between anatomical features of the grayscale ultrasound image and color Doppler markers of the ultrasound transmitters of the instrument(s). In some embodiments, the color Doppler markers can be used to determine the location and/or shape of an anatomical structure the device was placed into (e.g., a blood vessel). In some embodiments, the ultrasound transmitters can be placed at specific locations of the minimally invasive device, and can be configured to generate color Doppler signals of different colors (e.g., based on different waveforms received from waveform generator 140) such that the color Doppler markers can be individually identified and used to determine the orientation of instrument 160 based on the known location of the transmitters on the instrument. Additionally or alternatively, in some embodiments, ultrasound transmitters can be placed at specific locations of the minimally invasive device, and can be configured to generate color Doppler signals of the same or different colors individually (e.g., by providing driving signals to particular individual transmitters, a user can identify a particular portion of the device to which the ultrasound transmitter is affixed).

In some embodiments, a user can adjust the parameters of waveform generator 140 (e.g., as described above in connection with 202) and/or adjust parameters of ultrasound imaging system 102 (e.g., as described above in connection with at 206) at 220 (and/or at any other suitable time). For example, a user can change the intensity of the color Doppler marker by adjusting the amplitude of the applied signal via the waveform generator. In such an example, the amplitude (e.g., peak-to-peak voltage) of the signal can be increased to compensate for signal losses due to attenuation in various propagation media (e.g., water generally produces minimal attenuation, more signal attenuation is observable in exposed open-chest heart scans, and much more signal attenuation is observed in a closed-chest setting). As another example, a user can change the color of the color Doppler marker by changing the frequency of the applied signal via the waveform generator. In some embodiments, the color Doppler marker can be increased in size and/or viewed differently (e.g., in a different color) by changing the color Doppler scale key on the ultrasound imaging system (e.g., limits, baseline, etc.).

Figure 3:
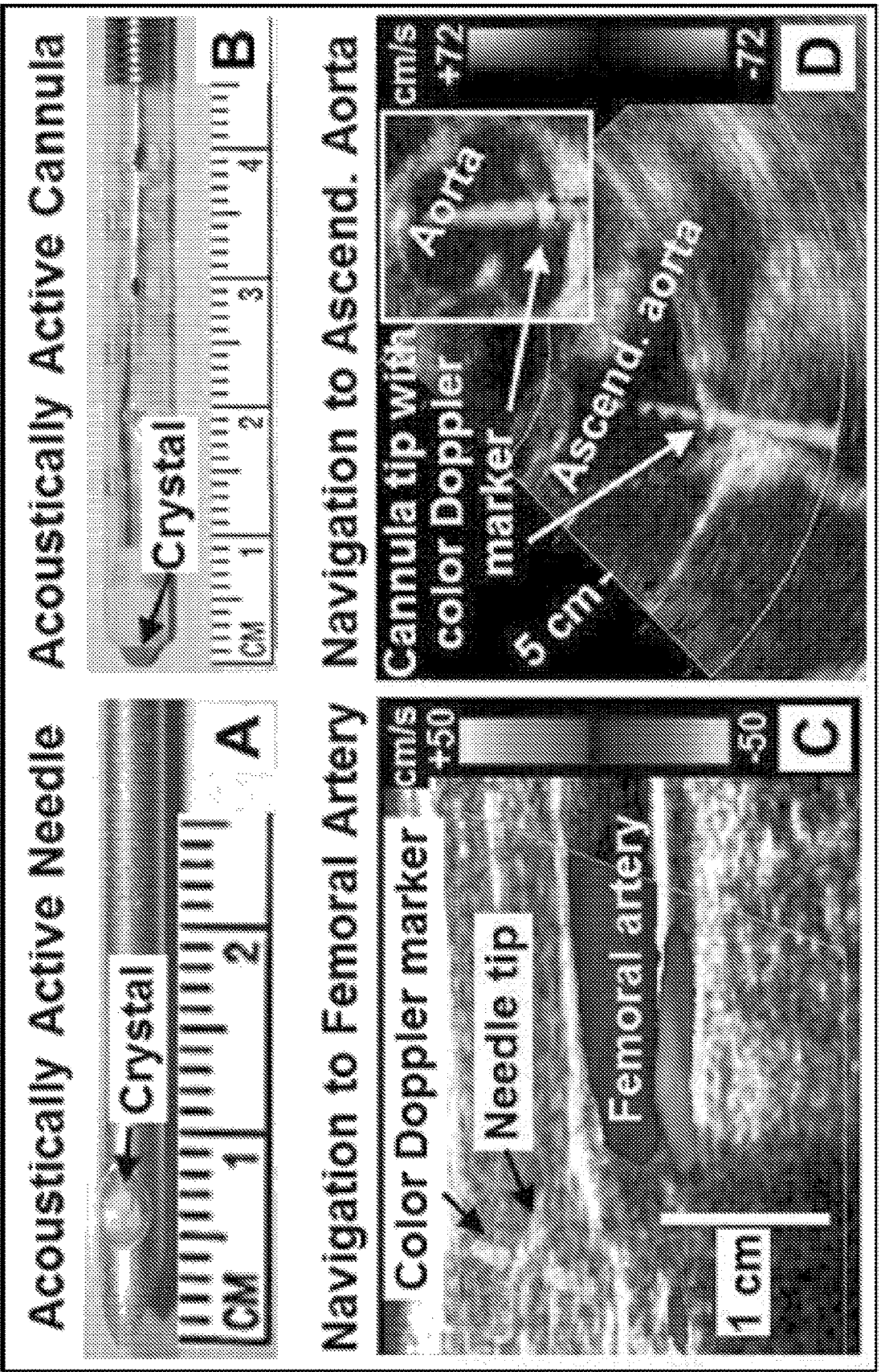
FIG. 3 shows examples of ultrasonic transmitters affixed to minimally invasive instruments implemented in accordance with some embodiments of the disclosed subject matter, and ultrasound images with markers overlaid on the image based on signals emitted from the ultrasonic transmitters.

FIG. 3 shows an example of an acoustically active needle (shown in the upper left portion marked A), an acoustically active cannula (shown in the upper right portion marked B), a color Doppler image showing the acoustically active regions (shown in the upper left portion marked C), and the navigation of an acoustically active cannula on a color Doppler image (shown in the upper left portion marked D).

Figure 4A:
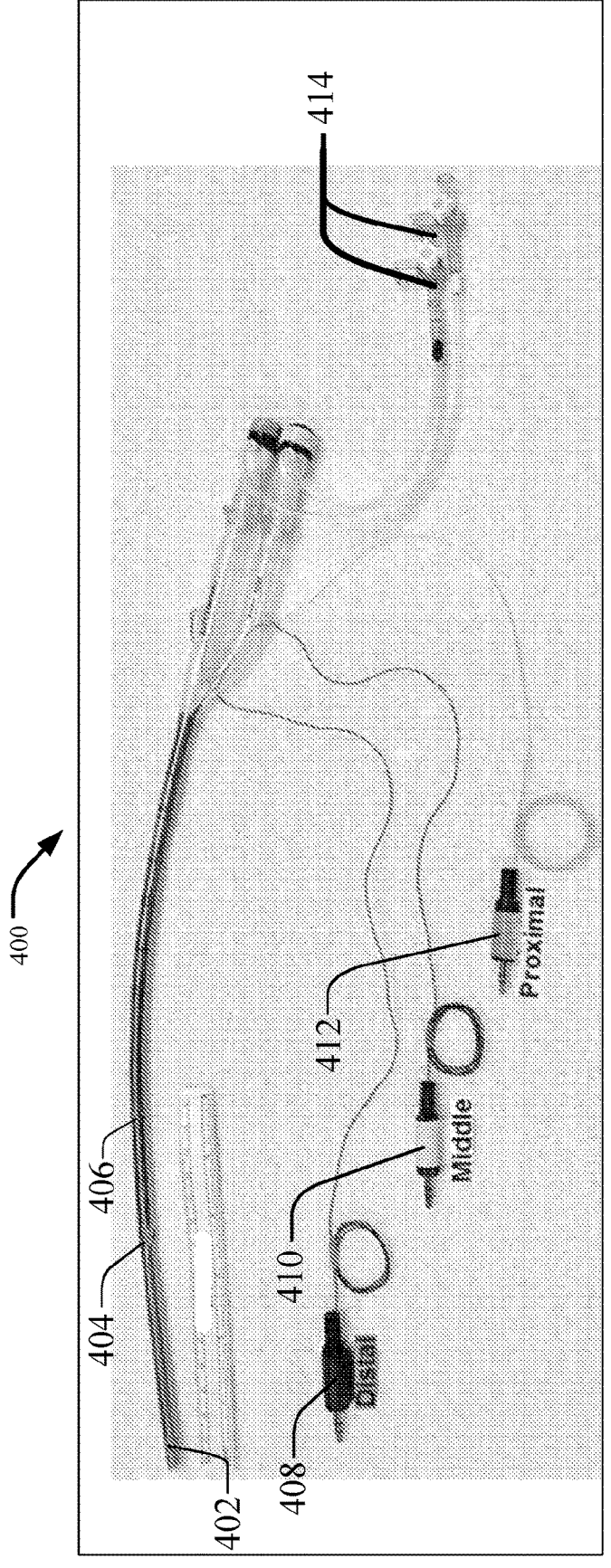
FIG. 4A shows an example of a cannula implemented using techniques described herein that can be used in connection with the system of FIG. 1 in accordance with some embodiments of the disclosed subject matter.
Figure 4B:
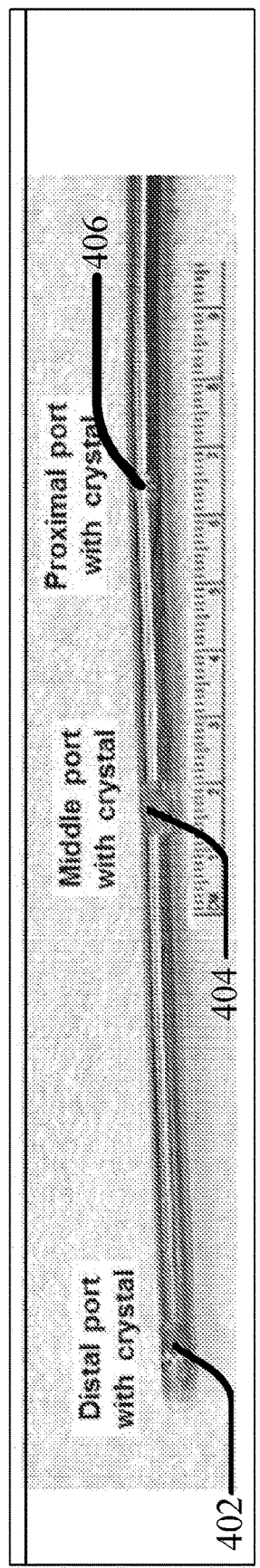
FIG. 4B shows a magnified photo of the ultrasonic transmitters that are affixed to the device ports shown in FIG. 4A.

FIG. 4A shows an example of an acoustically active cannula 400, which is an example of an instrument that can be used in some embodiments of the disclosed subject matter. Specifically FIG. 4A shows an example of an entire active cannula 400, in which ultrasound transmitters 402, 404, and 406 are affixed to the commercially available device. Additionally or alternatively, lead 408 is electrically connected to ultrasound transmitter 402, lead 410 is electrically connected to ultrasound transmitter 404, and lead 412 is electrically connected to ultrasound transmitter 406. The leads 408, 410, and 412 are configured to be electrically connected to the waveform generator. Infusion line connector(s) 414, include two conduits that can be used to introduce a fluid through active cannula 400. For example, a fluid can be introduced through one line connector, flow through a conduit inside the cannula, and exit through a related delivery port (sometimes referred to herein as an orifice), for example, the orifice associated with ultrasound transmitter 404 is attached. Whereas, a line connection, conduit, and related orifice associated with ultrasound transmitters 402 and 406, can be used to drain fluid from a subject (e.g., blood). FIG. 4B shows a magnified portion of the acoustically active cannula. The specific placement of the ultrasonic transmitters (e.g., implemented using piezoelectric crystals) can be seen on the cannula. In the magnified view FIG. 4B, ultrasound transmitter 402 is placed in a distal position, ultrasound transmitter 404 is placed in a middle position, and ultrasound transmitter 406 is placed in a proximal position.

In the example shown in FIGS. 4A and 4B, instrument 400 is an acoustically active endovenous extracorporeal membrane oxygenation (ECMO) cannula (cannula) that has two separate lumens (e.g., coupled to infusion line connector(s) 414). The first lumen is connected with the proximal and distal ports for venous blood drainage from the superior vena cava (SVC) and inferior vena cava (IVC), respectively. The second lumen is connected to the middle orifice and can be used to deliver oxygenated blood to the right atrium (RA). The three orifices on the cannula were made acoustically active by affixing round piezoelectric crystals that are 1 to 3 millimeters (mm) in diameter. The crystals are embedded and glued to the cannula in such a way that patency of each orifice is preserved. In this example, up to two crystals at a time can be connected to a 2-channel waveform generator (e.g., an AGILENT 33500B; Agilent Technologies™, Loveland, Colorado) with a 33 to 42-gauge double-conductor stranded wire and continuously driven by a square-wave voltage signal with a frequency of 100 kHz to 103 kilohertz (kHz) and 0.3 to 3.0 peak-to-peak voltage (Vpp). The ultrasound transmitters (piezoelectric crystals) can be driven by a voltage waveform at a specific frequency, for a specified period of time (e.g., on/off during certain checkpoints of a procedure, and/or off in order to complete a different imaging sequence) to generate color Doppler markers that can be used to locate the ports on an ultrasound image.

Figure 5:
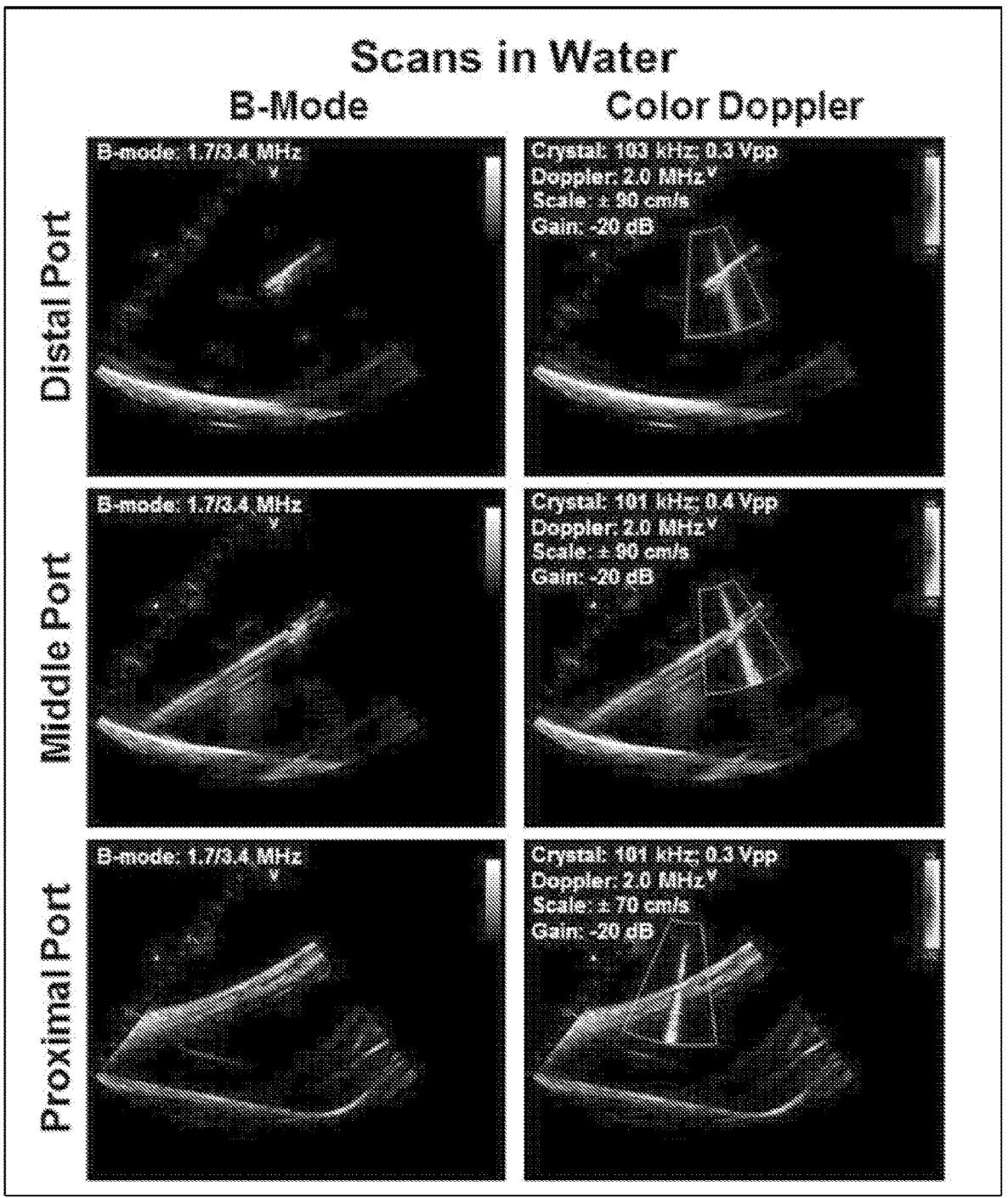
FIG. 5 shows an example of an ultrasound image depicting a cannula in water generated using a system implemented in accordance with some embodiments of the disclosed subject matter.

FIG. 5 shows an example of B-Mode ultrasound images of the acoustically active instrument in water in the left panels, and corresponding color Doppler images of the acoustically active instrument in water in the right panels. More specifically, FIG. 5 shows the distal, middle, and proximal ports of the cannula in B-mode imaging (left panels) and in color Doppler mode imaging with the color marker active (right panels) under optimal scanning conditions (i.e., in water). As shown in FIG. 5, in the B-mode scans in the left panels the cannula orifices are not easily (or not at all) identifiable, whereas the ports can be clearly identified by specific color markers in real-time color Doppler scans in the right panels. Combinations of the driving frequency at 101 or 103 kHz with a color scale set to ±70 or ±90 centimeters per second (cm/s) produced Doppler markers with red, blue, and yellow colors that distinctly identified the distal, middle, and proximal ports, respectively. The locations of individual ports would not be identifiable in conventional B-mode scans (e.g., as shown in the left panels). In this example, the Doppler gain was set to −20 dB, which omitted color blood flow patterns if the cannula was being imaged in vivo. The voltage amplitude was set to 0.3 or 0.4 Vpp to drive the embedded crystals and to produce clearly visible markers (including decreasing the Doppler gain).

Plain B-mode imaging did not allow for visual localization of the ports on the cannula, even though the identification and optimal placement of the cannula is important due to the different functional roles of the ports (i.e., blood drainage vs delivery). Moreover, the cannula is indistinguishable if the cannula has similar echogenicity with its surrounding tissue. The activation of one crystal at a time, or using a unique marker color, allows for easy identification of a specific orifice in conjunction with color Doppler imaging.

Figure 6:
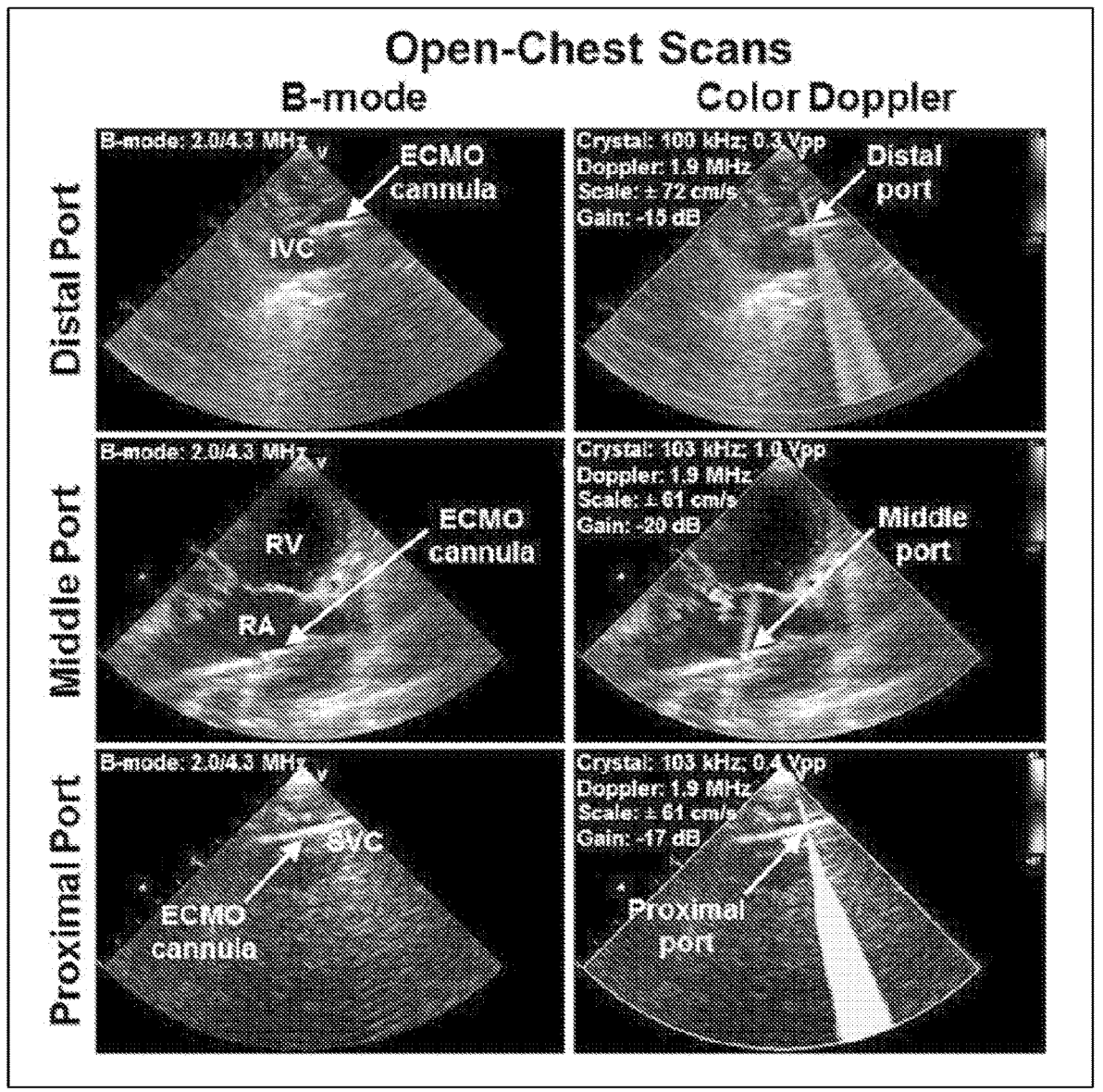
FIG. 6 shows examples of open-chest transthoracic ultrasound images of a cannula inserted into a pig heart generated using a system implemented in accordance with some embodiments of the disclosed subject matter.

FIG. 6 shows an example of open-chest epicardial scans in a pig. The left upper panel shows a B-mode ultrasound image of the acoustically active instrument. The right upper panel shows the corresponding color Doppler image of the acoustically active instrument. Additionally, FIG. 6 shows scans obtained by B-mode (left panels) and color Doppler (right panels). Identification of the cannula tip, where the distal orifice is located, is straightforward in the right upper panel scans due a blue color marker The blue marker visually pinpoints the location of the distal orifice on the cannula tip. The presence of the marker can be used to verify that the depicted cannula tip is real and not a false positive image of the cannula. The middle and proximal ports are indistinguishable in the B-mode scans (left panels) due to a lack of a reference point on the cannula (e.g., the cannula tip was a useful reference point for the distal orifice in the left upper B-mode scan). Different color markers were used for the color Doppler image, including red and yellow to identify and optimize position of the middle and proximal ports in the RA (right atrium) and SVC (superior vena cava), respectively. The epicardial scans in a pig with an interposed attenuating pad (simulating attenuation of a human chest) were comparable in imaging quality to human clinical transthoracic echocardiography scans. The Doppler gain was set to −15 to −20 dB for consistency with transthoracic studies and scans in water, and to minimize or eliminate depiction of the blood flow by color Doppler in IVC, SVC, RA, and RV (right ventricle).

Figure 7:
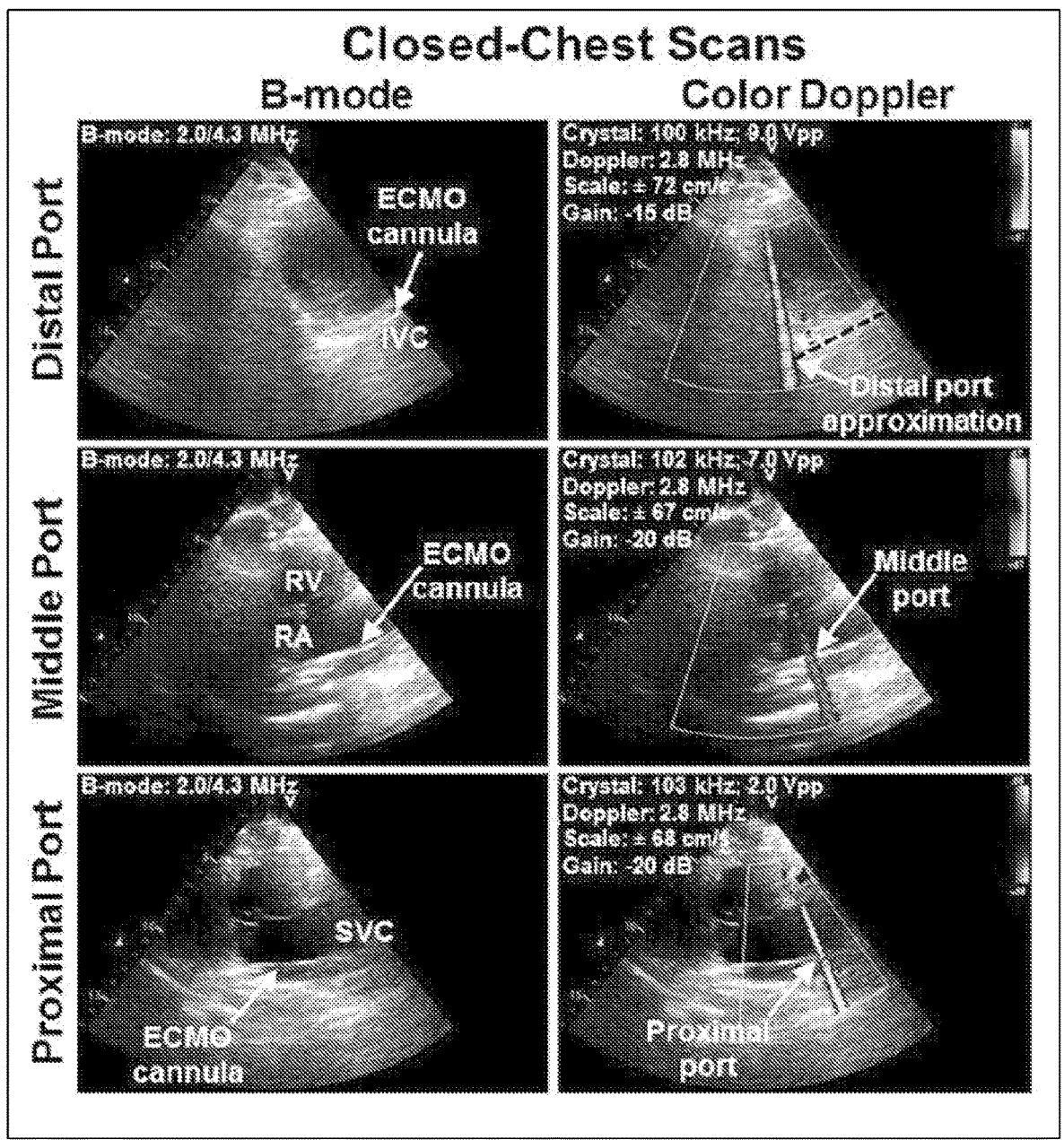
FIG. 7 shows a closed-chest transthoracic ultrasound image of a cannula inserted into a pig heart using a system implemented in accordance with some embodiments of the disclosed subject matter.

FIG. 7 is analogous to FIG. 6; however, it shows B-mode (left panels) and color Doppler (right panels) images obtained by transthoracic scans in pigs. The resulting scans are of relatively poor quality due to the attenuating effect of the animal's chest wall. This setting simulates limited-quality clinical scans occurring in some human patients. The cannula is barely recognizable in B-mode scans (left panels), and the distal orifice had to be approximated. Consequently, the color Doppler markers (right panels) for each orifice can serve multiple purposes. First, the mere occurrence of the marker indicates the presence of the corresponding orifice within the Doppler scan plane. Second, the marker can be used to guide the particular orifice identified within the scan plane to the appropriate anatomic location. The Doppler gain was set to −15 to −20 dB for consistency with open-chest studies and scans in water. The driving signal amplitude ranged from 2.0 to 9.0 Vpp.

In some embodiments, the color Doppler scans in FIG. 6 (right panels) match both the size and shape of the underlying B-mode images. Therefore, a full length of the marker along the interrogating Doppler beam is displayed. For comparison, color Doppler scans in FIGS. 5 and 7 (right panels) approximate more closely the location of the cannula. As a result, the Doppler scan size is smaller and, therefore, the elongated color markers appear shorter and are centered across the cannula at the location of the particular port.

Experimental Tests

In an example system, some of the mechanisms described herein were implemented using a Vivid 7 (GE Healthcare, Chicago, Illinois) ultrasound system and an M4S phased array sector probe (GE Healthcare) set to harmonic B-mode imaging at 1.7/3.4 MHz or 2.15/4.30 (transmit/receive) frequencies. In color Doppler settings, emitted frequencies from 1.9 to 2.8 MHz were used, and the gain setting was between −20 and −15 dB. The negative gain setting reduced or eliminated the imaging of blood flow patterns in vivo, while preserving display of the color Doppler marker. The Doppler color velocity scale ranged from ±61 to ±90 cm/s, and a conventional red/orange and blue/cyan color map was used during acquisition. Digitally recorded echocardiography scans were transferred in a Digital Imaging and Communications in Medicine (DICOM) format to a computer with EchoPAC software (GE Healthcare) and converted to a video format. The EchoPAC software also allows for offline adjustments to the Doppler color map and color velocity scale (i.e., after imaging is complete). This feature was used to make the color markers for the distal, middle, and proximal ports blue, red, and yellow, respectively, for consistency of appearance in different experimental settings presented in FIGS. 5-7.

The color Doppler marker was tested in three different experimental settings: 1) in vitro in a water container, which represented optimal scanning conditions; 2) in vivo in an open-chest pig, which simulated realistic clinical scanning conditions; and 3) in vivo in a closed-chest pig, which replicated limited transthoracic clinical scans. The animal studies were approved by the Mayo Institutional Animal Care and Use Committee. The cannula was placed in a 3-gallon container padded with a sound-absorbing layer and filled with degassed water. During image acquisition, the cannula ports were subsequently centered within a 14-cm-deep sector scanning field. The open-chest study was performed in a pig weighing 80 kg. The animal was intubated, mechanically ventilated (Narkomed 6000; Draeger Inc, Telford, PA, USA), fully anesthetized with inhalation isoflurane and intravenous fentanyl, and placed in the supine position. The chest of this animal was open by mid-sternotomy and the heart placed on a pericardial cradle. An attenuated urethane pad was interposed between the transducer face and epicardial surface during ultrasound scans. The interposed urethane pad induced an approximately 8-dB signal loss and mimicked ultrasound signal attenuation caused by a human chest during clinical echocardiographic studies. The closed-chest study was performed on a pig weighing 87 kg. The animal was intubated, ventilated, and anesthetized as described above. Transthoracic parasternal or atypical echocardiographic projections were used for obtaining views of the RA and the adjacent segments of the IVC and SVC. Transthoracic scans in an adult pig are technically difficult and of poor imaging quality due to narrow intercostal spaces and oval configuration of the chest. Ultrasound gel was used in both animal studies to assure acoustic coupling of the transducer.

The cannula was inserted through the right jugular vein. The insertion was guided by B-mode imaging combined with color Doppler imaging, to produce an instantaneous marker for identification of each of the three cannula ports as needed. The color Doppler marker was generated as follows: Each crystal embedded into the cannula (e.g., as shown in FIG. 3) can be individually connected to the waveform generator to vibrate and produce an acoustic field containing high frequency harmonics. The harmonics interact with the transmitted Doppler imaging signal. This interaction results in a new signal that is received by the echocardiography system and interpreted as a Doppler shift. Consequently, an instantaneous color marker is displayed on the ultrasound system screen (e.g., as described above in connection with FIGS. 5-7). This marker tracks a position of the vibrating crystal within a color Doppler scan plane and identifies the specific orifice to which the crystal is attached on the cannula. Changes in the driving signal frequency or color velocity scale and map settings determine the color of the marker, which can then be made unique for each identified port.

This experimental study demonstrated that an acoustically active cannula can be guided by conventional color Doppler echocardiography under optimal, clinically realistic, and limited imaging conditions. Display of an instantaneous color Doppler marker enables straightforward identification of each of the three ports on the cannula and their real-time tracking for optimal placement within cardiovascular anatomy.

In its conventional application, color Doppler echocardiography identifies motion direction of the myocardium (sometimes referred to as tissue Doppler imaging) or blood (sometimes referred to as flow Doppler imaging), and measures mean and variance of tissue or blood velocity. Such measurements are typically presented as color coded velocity maps that are superimposed, in real time, over B-mode scans.

In some embodiments, using techniques described herein can facilitate using color Doppler imaging to guide procedures that involve insertion of instruments into within a subject's body. The ability of an ultrasound system to simultaneously generate B-mode and color Doppler images is unaffected, and any color flow Doppler-capable ultrasound machine can be used for the guidance approach. During image guidance, visualization of color-coded blood flow velocities is subdued by decreasing the Doppler gain, so that only the color marker identification and tracking of the specific orifice on the cannula is displayed. However, this is merely an example, and blood flow velocity imaging can also be presented within the same scanning projection by setting the Doppler gain to a conventional level. Combining color Doppler flow and guidance scans can be used to verify that intravascular blood flow is preserved and to verify positioning of the cannula. For example, the cannula shown in FIG. 3 is a relative complex instrument (e.g., including two lumens and three ports for blood drainage and/or delivery of one or more gases and/or fluids).

In the animal studies, the generation of the color marker and its role in clinically realistic scanning conditions (e.g., as described above in connection with FIG. 5) and in highly challenging limited imaging conditions (e.g., as described above in connection with FIG. 7), was tested. The identification of the related distal, middle, or proximal port. In the limited conditions, poor depiction of the cannula in B-mode scans often precludes even determination of whether the cannula is within the scan plane or not, whereas out-of-plane motion of the cannula due to cardiac or respiratory cycling was noticeable when using techniques described herein, because the color marker vanished from the displayed projection of the heart or vessel. For this example, only one piezoelectric crystal was activated at a time using the available two-channel waveform generator, to display an instantaneous marker for the specific orifice on the cannula. In some embodiments, a multi-channel waveform generator could be used to supply two different crystals with alternative waveforms at a time. Different waveforms can display multiple specific markers with distinctive colors within one scan plane. These strategies reduced any potential difficulty with identifying the specific orifice even in limited quality transthoracic scans in the experimental pigs.

The signal amplitude in closed-chest studies (e.g., as described above in connection with FIG. 7) was approximately 10 times higher than open-chest scans conducted with an interposed attenuating pad (e.g., as described above in connection with FIG. 7). The higher signal amplitude in the closed-chest studies was used to compensate for greater signal attenuation through the pig chest. The Doppler gain was set to −15 to −20 dB in closed-chest scans for procedural consistency. Increasing the gain during closed-chest scans would considerably enhance the markers and, consequently, allow for the use of lower voltages for driving embedded crystals. However, flow patterns in the IVC, SVC, RA, and RV would then occur and visually mask the markers. Online or offline changes can be made to the color map and color velocity scale of the Doppler scans. Adjustments in frequency of the crystal-driving signal can be used to customize the instantaneous marker color. Additionally or alternatively, different colors can be associated with different ports on the same cannula to individually identify the ports during a procedure.

Techniques described herein can facilitate a new use for broadly available conventional color Doppler echocardiography machines as spatial navigation tools, specifically because no hardware or software modifications to the ultrasound imaging system are needed. Moreover, the color marker displayed by the color Doppler machine is robust in identifying a particular orifice and/or any other feature, such as a specific location on an instrument) and tracking its location in all tested imaging conditions. Each instantaneous color Doppler marker produced by one of the piezoelectric crystals embedded in the acoustically active cannula can serve multiple purposed. For example, a sole occurrence of the marker on the echocardiography screen alerts users that the vibrating crystal (and thus the related port) is located within the imaging scan plane. This can be especially useful in limited-quality scans. As another example, the marker identifies the specific orifice of the cannula. As yet another example, the color marker can facilitate real time guidance of a particular orifice toward a specific anatomic position.

Acoustic interactions of an embedded vibrating crystal with an interrogating Doppler beam produce an instantaneous color marker that is visible even under limited echocardiographic scanning conditions. In an experimental setting, the marker distinctly identified drainage and delivery ports of the acoustically active cannula and guides them reliably to their desired anatomic locations. The techniques described herein can open up a new role for color Doppler ultrasonography as an imaging guidance technique and translate into the development of a variety of acoustically active tools for ultrasound-guided minimally invasive interventions.

It should be noted that, as used herein, the term system can encompass hardware, software, firmware, or any suitable combination thereof.

It should be understood that the above described steps of the process of FIG. 2 can be executed or performed in any order or sequence not limited to the order and sequence shown and described in the figures. Also, some of the above steps of the process of FIG. 2 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. An ultrasound guidance system comprising:
a medical instrument having a first ultrasound transmitter and a second ultrasound transmitter coupled to the medical instrument, wherein the first ultrasound transmitter and the second ultrasound transmitter are arranged on the medical instrument and fixed relative to each other with a known spatial relationship;
a waveform generator in communication with the first ultrasound transmitter and the second ultrasound transmitter, the waveform generator configured to:
drive the first ultrasound transmitter with a first electrical waveform, the first electrical waveform including a first square wave,
drive the second ultrasound transmitter with a second electrical waveform, the second electrical waveform including a second square wave,
wherein driving the first ultrasound transmitter with the first electrical waveform causes the first ultrasound transmitter to generate a first acoustic signal, the first acoustic signal having multiple frequency components,
wherein driving the second ultrasound transmitter with the second electrical waveform causes the second ultrasound transmitter to generate a second acoustic signal, the second acoustic signal having multiple frequency components, and
wherein the waveform generator simultaneously drives both the first ultrasound transmitter and the second ultrasound transmitter; and
a processor configured to:
generate a first color Doppler marker based on an interaction of the first acoustic signal with an ultrasound beam,
generate a second color Doppler marker based on an interaction of the second acoustic signal with the ultrasound beam, and
determine a location and an orientation of the medical instrument based on the first color Doppler marker, the second color Doppler marker, and the known spatial relationship between the first ultrasound transmitter and the second ultrasound transmitter.

2. The ultrasound guidance system of claim 1, wherein the first electrical waveform is a square wave having a duty cycle in a range of 25% to 75%.

3. The ultrasound guidance system of claim 2, wherein the first electrical waveform has a frequency in a range from 90 to 110 kHz.

4. The ultrasound guidance system of claim 2, wherein the first electrical waveform has an amplitude in the range from 0.3 to 9.0 volts peak to peak (Vpp).

5. The ultrasound guidance system of claim 1, wherein the medical instrument is a cannula that has a first port, and a second port, and
wherein the first ultrasound transmitter is associated with the first port, and the second ultrasound transmitter is associated with the second port.

6. The ultrasound guidance system of claim 5, wherein the cannula has a third port, and a third ultrasound transmitter is associated with the third port, the third ultrasound transmitter being in communication with the waveform generator.

7. The ultrasound guidance system of claim 6, wherein the third ultrasound transmitter is arranged relative to the first ultrasound transmitter and the second ultrasound transmitter with another known spatial relationship, and:
the waveform generator is configured to:
drive the third ultrasound transmitter with a third electrical waveform, the third electrical waveform being a square wave,
wherein driving the third ultrasound transmitter with the third electrical waveform causes the third ultrasound transmitter to generate a third acoustic signal, the third acoustic signal having multiple frequency components; and
the processor is configured to:
generate a third color Doppler marker based on an interaction of the third acoustic signal with the ultrasound beam, and
determine the location and the orientation of the medical instrument based on the first color Doppler marker, the second color Doppler marker, the third color Doppler marker, the known spatial relationship, and the other known spatial relationship.

8. The ultrasound guidance system of claim 7, wherein the first, second, and third electrical waveforms each have a waveform frequency, wherein at least two or more of the waveform frequencies are different.

9. The ultrasound guidance system of claim 7, wherein the first, second, and third electrical waveforms each have a waveform amplitude, wherein at least two or more of the waveform amplitudes are different.

10. An ultrasound guidance system comprising:
a waveform generator in communication with a first ultrasound transmitter and a second ultrasound transmitter of an instrument, wherein the first ultrasound transmitter and the second ultrasound transmitter are arranged on the instrument and fixed relative to each other with a known spatial relationship;
an ultrasound machine comprising:
a display;
an ultrasound transducer configured to emit a first color Doppler signal; and
at least one processor that is configured to:
cause the waveform generator to drive the first ultrasound transmitter with a first electrical waveform during navigation of the instrument, the first electrical waveform being a square wave, wherein driving the first ultrasound transmitter with the first electrical waveform causes the first ultrasound transmitter to generate a first acoustic signal, the first acoustic signal having multiple frequency components;
cause the waveform generator to drive the second ultrasound transmitter with a second electrical waveform during navigation of the instrument, the second electrical waveform being a square wave, wherein driving the second ultrasound transmitter with the second electrical waveform causes the second ultrasound transmitter to generate a second acoustic signal, the second acoustic signal having multiple frequency components;
cause the ultrasound transducer to emit the color Doppler signal;
detect a interacted acoustic signal from the ultrasound transducer, the first interacted acoustic signal being formed by an interaction between the first acoustic signal and the first color Doppler signal, the first interacted acoustic signal being used to form a first color Doppler marker;

detect a second interacted acoustic signal from the ultrasound transducer, the second interacted acoustic signal being formed by an interaction between the second acoustic signal and the color Doppler signal, the second interacted acoustic signal being used to form a second color Doppler marker;

generate a first ultrasound image that includes the first color Doppler marker and the second color Doppler marker using the display;

determine a location and an orientation of the instrument based on the first color Doppler marker and the second color Doppler marker depicted in the first ultrasound image and the known spatial relationship between the first ultrasound transmitter and the second ultrasound transmitter; and cause the first ultrasound image to be displayed using the display, wherein the waveform generator simultaneously drives both the first ultrasound transmitter and the second ultrasound transmitter.

11. The ultrasound guidance system of claim 10, wherein the ultrasound machine has a gain parameter that controls amplification of the detected second color Doppler signal; and wherein the gain parameter is set in a range from −20 decibels (dB) to −15 dB.

12. The ultrasound guidance system of claim 10, wherein the ultrasound transducer is configured to emit a first brightness mode (B-mode) acoustic signal, and to receive a second B-mode acoustic signal, and wherein the at least one processor is configured to:

generate the first ultrasound image based on the first color Doppler marker and the second B-mode acoustic signal; and cause the first ultrasound image to be displayed using the display.

13. The ultrasound guidance system of claim 10, wherein the processor is configured to adjust the color of the first color Doppler marker by adjusting the frequency of the first electrical waveform.

14. The ultrasound guidance system of claim 10, wherein the processor is configured to adjust the size of the first color Doppler marker by adjusting the amplitude of the first electrical waveform.

15. A method for detecting and guiding a medical instrument, the method comprising:

outputting a first electrical waveform while the medical instrument is guided, the first electrical waveform being a square wave;

outputting a second electrical waveform while the medical instrument is guided;

generating a first acoustic signal based on the first electrical waveform using a first ultrasound transmitter coupled to the medical instrument;

generating a second acoustic signal based on the second electrical waveform using a second ultrasound transmitter coupled to the medical instrument fixed relative to the first ultrasound transmitter with a known spatial relationship relative to the first ultrasound transmitter;

generating a color Doppler signal with an ultrasound transducer;

receiving a first interacted acoustic signal with the ultrasound transducer, the first interacted acoustic signal being formed from the interaction between the first acoustic signal and the color Doppler signal;

receiving a second interacted acoustic signal with the ultrasound transducer, the second interacted acoustic signal being formed from the interaction between the second acoustic signal and the color Doppler signal;

generating a first color Doppler marker based on the first interacted acoustic signal;

generating a second color Doppler marker based on the second interacted acoustic signal;

generating an ultrasound image that includes the first color Doppler marker and the second color Doppler marker; and determining a location and an orientation of the medical instrument based on the first color Doppler marker and the second color Doppler marker depicted in the ultrasound image and the known spatial relationship between the first ultrasound transmitter and the second ultrasound transmitter, wherein the first acoustic signal and the second acoustic signal are generated simultaneously.

16. The method of claim 15, wherein generating the first acoustic signal comprises driving an ultrasound transducer with a square wave.

* * * * *